United States Patent [19]

Battistini et al.

[11] Patent Number: 5,374,626
[45] Date of Patent: Dec. 20, 1994

[54] 5'-ALKYLPHOSPHONYLNUCLEOSIDES AS ANTIVIRALS

[75] Inventors: Carlo Battistini, Novate Milanese; Giovanni Franceschi, Milan; Domenico Ungheri, Parabiago; Maria A. Verini; Sergio Vioglio, both of Milan, all of Italy

[73] Assignee: Farmitalia Carlo ERBA, Milan, Italy

[21] Appl. No.: 38,331

[22] Filed: Mar. 12, 1993

Related U.S. Application Data

[63] Continuation of Ser. No. 688,948, filed as PCT/EP90/01602, Sep. 20, 1990, abandoned.

[30] Foreign Application Priority Data

Sep. 22, 1989 [GB] United Kingdom ........... 8921469

[51] Int. Cl.$^5$ ........................................... A61K 31/70
[52] U.S. Cl. ........................ 514/47; 536/26.5; 536/26.7
[58] Field of Search .............. 536/26.21, 26.7; 514/47

[56] References Cited

U.S. PATENT DOCUMENTS

| | | | |
|---|---|---|---|
| 3,560,478 | 2/1971 | Myers | 536/26.21 |
| 4,469,863 | 9/1984 | Tso et al. | 536/24.5 |
| 4,500,707 | 2/1985 | Caruthers et al. | 536/25.34 |

FOREIGN PATENT DOCUMENTS

| | | | |
|---|---|---|---|
| 0190726 | 8/1986 | European Pat. Off. | 536/26.7 |
| 0097376 | 1/1988 | European Pat. Off. | 536/26.7 |
| 0272446 | 6/1988 | European Pat. Off. | 558/70.0 |

OTHER PUBLICATIONS

Agris et al., "Inhibition of Vesicular Stomatitis Virus Protein Synthesis and Infection by Sequence-Specific Oligodeoxyribonucleoside Methylphosphonates," *Biochemistry*, 25, 6268–6275 (1986).

Marugg et al., "Synthesis of Nucleic Acid Methylphosphonates Via the 1-Hydroxybenzotriazole Phosphotriester Approach," *Nucleic Acids Research*, 14(5), 2171–2185 (1986).

Puech et al., "Synthesis and Biological Evaluation of Isomeric Dinucleoside Monophosphates and Monomethylphosphonates of 9-β-D-Arabinofuranosyladenine and Related Analogues," *J. Med. Chem.*, 31, 1897–1907 (1988).

Kosolapoff et al., "Organic Phosphorus Compounds," vol. 4, Wiley–Interscience, New York, 1972, pp. 269, 269 and 288.

Kochetkov et al., *Organic Chemistry of Nucleic Acids,* Part A, Plenum Press, New York, 1971, pp. 65–66.

Jager et al., "Synthesis of Methylphosphonate and Methylphosphotriester Analogues of 2',5'-Adenylate Trimers," *Nucleic Acids Research Symposium Series,* No. 9, IRL Press, Ltd. London, 1981, pp. 149–152.

Santi et al., "Tyrosyl Transfer Ribonucleic Acid Synthetase from *E Coli* B. Analysis of Tyrosine and Adenosine 5-Triphosphate Binding Sites," *J. Med. Chem.,* 16(3), 277–280 (1973).

(List continued on next page.)

*Primary Examiner*—John W. Rollins
*Attorney, Agent, or Firm*—Oblon, Spivak, McClelland, Maier & Neustadt

[57] ABSTRACT

The present invention relates to the use as antivirals of compounds of formula:

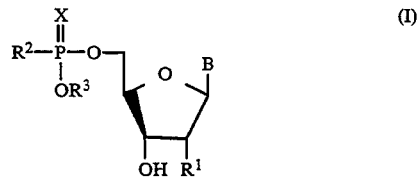

wherein B is a purinic or pyrimidinic heterocycle; X is oxygen or sulphur; $R^1$ is a hydroxyl group or a hydrogen atom; $R^2$ is a linear, branched or cyclic, alkyl group of up to twenty carbon atoms; $R^3$ is as specified for $R^2$ above or a hydrogen atom, a cation or a polyhydroxy group.

7 Claims, No Drawings

OTHER PUBLICATIONS

Griengl et al., "Phosphonoformate and Phosphonoacetate Derivatives of 5-substituted-2'-deoxyuridines: Synthesis and Antiviral Activity," *J. Med. Chem.*, 31(9), 1831–1839 (1988).

Lambert et al., "Synthesis and Antiviral Activity of Phosphonoacetic and Phosphonoformic Acid Esters of 5-Bromo-2'-deoxyuridines and Related Pyrimidine Nucleosides and Acylclonucleosides," *J. Med. Chem.* 32(2), 367–374 (1989).

Journal of Medicinal Chemistry, vol. 16, No. 3, Mar. 1973, D. V. Santi et al.: "Tyrosyl transfer ribonucleic acid synthetase from escherichia coli B".

Journal of Medicinal Chemistry, vol. 31, No. 9, Sep. 1988, H. Griengl et al. : "Phosphonoformate and phosphonoacetate derivatives of 5-substituted 2'-deoxyuridines: synthesis and activiral activity", pp. 1831–1839, see the whole document Journal of Medicinal Chemistry, vol. 32, No. 2, Feb. 1989, R. W. Lambert, et al.: "Synthesis and antiviral activity of phosphonoacetic and phosphonoformic acid esters of 5-bromo-2-deoxyuridine and related pyrimidine nucleosides and acyclonucleosides": , pp. 367–374, see the whole document.

5'-ALKYLPHOSPHONYLNUCLEOSIDES AS ANTIVIRALS

This application is a continuation of application Ser. No. 07/688,948, filed as PCT/EP90/01602, Sep. 20, 1990, now abandoned.

The present invention relates to the use as antivirals of compounds of formula I:

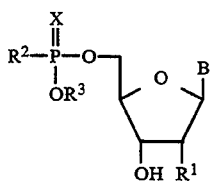

wherein B is a purine or pyrimidine heterocycle; X is oxygen or sulphur; $R^1$ is a hydroxyl group or a hydrogen atom; $R^2$ is a linear, branched or cyclic alkyl group of up to twenty carbon atoms; $R^3$ is a group as specified for $R^2$ above or a hydrogen atom, a cation or a polyhydroxy group. The heterocycles which B may represent include adenine, guanine, cytosine, thymine and uracil or derivatives thereof such as 5-methyl uracil or 5-methylcytosine; B preferably represents adenine.

$R^2$ is typically a linear or branched alkyl group of 1 to 6 carbon atoms, usually of 1 to 4 carbon atoms. Preferably $R^2$ is a methyl, ethyl, propyl, isopropyl or n.butyl group. The cations which $R^3$ may represent include alkali metal cations e.g. sodium, or potassium, and cations such as ammonium and alkylammonium cations in which the alkyl group may be linear, branched or cyclic and is preferably of 1 to 6 carbon atoms, more preferably 1 to 4 carbon atoms; the expression "polyhydroxy group" in the definition of $R^3$ encompasses a glyceryl or carbohydrate residue, such as a mono- or di- saccharide, or a ketoderivative. Some of the compounds of formula I are already known, such a 5'-methylphosphonyladenosine which has previously been synthesized and tested for its hypotensive activity (U.S. Pat. No. 3,560,478) or used as a substrate for an enzyme. Nevertheless for none of the compounds has an antiviral use ever been described or claimed. The present compounds are broad spectrum antivirals being biologically active against several types or viruses, particularly RNA viruses. Compounds of formula I can be prepared directly from an unprotected deoxyribonucleoside or ribonucleoside like adenosine by phosphonylation with the appropriate alkylphosphonyldichloride at low temperature, preferably 0° C., using trialkylphosphate (generally trimethyl or triethylphosphate) as a solvent. After stirring the mixture at low temperature for one to ten hours, preferably about 6 h, the reaction is quenched by adding an aqueous solution of triethylammonium bicarbonate e.g. 0.1M. In this case the isolation of the reaction product is better performed by percolating the solution through an appropriate anion-exchange resin such as IRA-93; after a suitable water washing, the product can be eluted with an aqueous basic or salt solution but more conveniently it is eluted with 0.1M aqueous triethylammonium bicarbonate (TEAB). The solution is evaporated to dryness, the residue is dissolved in water and passed through a column containing the sodium form of a cation-exchange resin, preferably Dowex 50W -X8 - Na+ form. The resulting aqueous solution is evaporated under vacuum or freeze-dried to give the sodium salt of the 5'-alkylphosphonate of the treated nucleoside.

An unprotected nucleoside can also be phosphonylated by the use of the freshly prepared alkylphosphonylditriazolide. This active phosphonylating agent is prepared by a known procedure from the corresponding dichloride and used in the form of the solution in which it is obtained.

In this case, solvents and reaction conditions differ from those in the previously described process. In a typical procedure a solution of the dry nucleoside in a proper dry solvent, preferably pyridine, is added to the dry solution of the alkylphosphonylditriazolide in acetonitrile. The reaction mixture is stirred at room temperature for a variable length of time depending on the nucleoside type, generally from half an hour up to 5 hours. The reaction mixture can be conveniently quenched with an aqueous solution of triethylammonium bicarbonate or alternatively with triethylamine in water-pyridine followed by treatment with an aqueous solution of sodium bicarbonate. If no deprotection is needed, the product of reaction being already the final compound, the aqueous solution is concentrated and the product purified by reverse phase column chromatography preferably by using LiChroprep RP-8. Cation-exchange with sodium ion, as already described, affords the final compound. The same phosphonylation procedure can be used for properly protected deoxyribonucleoside or ribonucleoside, the protection being at the base and at the secondary hydroxyl 5 groups or only at the last ones. Starting from a ribonucleoside like adenosine, treatment with carbonyldiimidazole in dry DMF for some hours at room temperature, followed by an usual aqueous phase-organic solvent work-up, affords the 2',3'-cyclic carbonate nucleoside that can be crystallized from diethylether. The same compound can be alternatively obtained by reaction of the ribonucleoside with diphenylcarbonate in dry DMF in the presence of a catalytic amount of phenol and heating the mixture at high temperature for the necessary period of time, preferably at 150° C. for 1h.

Dilution of the mixture with diethylether causes the precipitation of the product.

The nucleoside, protected at the 2' and 3' positions as cyclic carbonate, can undergo the phosphonylation reaction with the ditriazolide derivative as described above and, after the reaction the 2',3'-protection is labile to the work-up conditions. Thus the process does not require any further deprotection step but only the final purification as described above for the unprotected nucleoside.

Other kinds of protection can be used for the hydroxyl groups at positions 2' and 3' of ribonucleosides or at position 3' of a deoxyribonucleoside.

For example the above described phosphonylation procedure can be applied to a 2',3'-0,0-bis(terbutyldimethylsilyl)ribonucleoside or to a 3'-0-terbutyldimethylsilyldeoxyribonucleoside, both of them easily obtainable from the corresponding unprotected nucleosides by known methodology. In these cases, a deprotection reaction preferably by using tetrabutylammonium fluoride in tetrahydrofuran is necessary after the phosphonylation step. Afterwards, purification of the final product can be performed as described above.

The phosphonylation reaction described above can also be applied to a ribonucleoside or a deoxyribonucleoside protected at the secondary hydroxyl groups and, if applicable, at the exocyclic amino group of the base with acyl groups such as benzoyl groups. An example of this case is described for 2',3'-0,0-6-N,N-tetrabenzoyladenosine prepared by standard procedures. Protection of the proper functional groups can be achieved also in a mixed mode by acyl and silyl groups like in 6-N-benzoyl-2',3'-0-(tetraisopropyldisiloxane-1,3-diyl) adenosine. In both the cases, after the alkylphosphonylation step is performed as described above, treatment with 30% ammonia in dioxane at room temperature for several hours is sufficient for a complete deprotection to give the final product.

For products further esterified at the phosphorus atom, the second esterifying group, generally a simple alkyl group, can be introduced successively to the alkylphosphonylation reaction either by adding the proper alcohol to the still active form of the 5'phosphonylated nucleoside before quenching the reaction mixture or by activating again the phosphonylated nucleoside with a suitable agent, for example DCC or carbonyldiimidazole.

Anyway better results are obtained by letting a bifunctional phosphonylating agent, like alkylphosphonyl-dichloride or alkylphosphonylditriazolide react first with an equimolar amount of the simpler alcohol and then making the resulting intermediate react directly with the proper nucleoside in the same reaction mixture. An example is described for 5'-0-(P-isopropyloxy-P-methyl-phosphonyl) adenosine.

The compounds of the formula I of the present invention have a broad spectrum antiviral activity particularly against RNA Viruses.

The antiviral activity was demonstrated in standard procedures which are more fully described hereinafter. The compounds were dissolved in an appropriate diluent which can be a buffer saline or Minimal Essential Medium or Tryptan phosphate broth or equivalent media.

The activity of the compounds was assessed both in in vitro and in vivo tests.

In vitro tests were carried out on monolayers of human Hep #2 cells infected with Respiratory Syncytial, Semliki Forest, Coxsackie and Vaccinia viruses, of hamster BHK cells infected with Columbia SK virus. The activity index (A.I.) was determined as the ratio: cytotoxicity, expressed as the concentration of the drug which determined a 50% decrease of cellular growth (Tissue Culture Inhibiting Dose 50% - T.C.I.D. 50), and the activity on infectious virus production, determined as the concentration which reduces by 50% the titre of virus in cell cryolysates. The results for 5'-methylphosphonate adenosine coded FCE 25148A are shown in table I.

The compounds of the formula I are also active in in vivo tests: for example on the pulmonitis caused by influenza virus and on the encephalitis experimental model of mice infected by Semliki Forest virus.

It is known that influenza virus, injected intranasally, induced in mice a pneumonia whose severity depends on the inoculum size: high doses cause death, low doses induce lung lesions whose extension can be evaluated by scores. If mice are infected with a sub-lethal dose of influenza and treated by the same route, lung lesions can be evaluated at the ninth day after killing them by cervical dislocation. Statistical significance of differences from the controls is evaluated by Wilcoxon test (1952). Results of a typical experiment are reported in table 2.

The activity of the compounds of the present invention on an encephalitis model can be determined by inoculating mice i.e. with Semliki Forest virus. For example the compounds were given i.c. in a volume of 30 ul of a suitable diluent. The results for FCE 25148A, reported in Table 3, are expressed as % mortality protection in comparison to the infected controls after 10 days post-infection.

Moreover, the compound FCE 25148A showed an antiviral activity against influenza and Semliki Forest much better than Ribavirin, that was used as the reference compound. The compounds of the present invention can be used to cure infections from the above mentioned virus and can be also used against other virus infections particularly from RNA viruses; special indications are the therapies of Toga, Bunja, Arena and other exotic viruses. In addition to the human viruses the compounds may be used against animal as well as plant viruses.

The compounds of the invention are useful in methods of treatment of the human or animal body by therapy. They have antiviral activity and can be used against RNA viruses in humans and other mammals. For this purpose, they can be formulated into oral dosage forms such as tablets, capsules and the like.

The present invention provides a pharmaceutical composition comprising as active ingredient a compound of formula (I) or a pharmaceutically acceptable base addition salt thereof, together with a pharmaceutically acceptable carrier or diluent.

The compounds can be administered alone or by combining them with a conventional carrier or diluent, such as magnesium carbonate, magnesium stearate, talc, sugar, lactose, pectin, dextrin, starch gelatin, tragacanth, methyl cellulose, sodium carboxymethyl cellulose, low melting wax, cocoa butter, and the like.

Flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart antiviral activity thereto on oral administration. The compounds may also be injected parenterally, in which case they are used in the form of a sterile solution containing other solutes, for example, enough saline or glucose to make the solution isotonic. Typically, a dose of 20–2000 mg of a compound of the invention may be administered per day to a human under treatment.

The compounds can be administered as an aerosol with particles small enough to reach the lower respiratory tract (mass median aerosol diameter $=1-2\mu$), and can be delivered via an oxygen hood or tent for treatment of severe lower respiratory tract infections due to respiratory syncytial virus or to other paramyxo or to myxoviruses.

The following examples illustrate the invention without limiting it.

EXAMPLE 1

Adenosine 5'-methylphosphonate sodium salt (FCE 25148A)

Preparation A

Triethylamine (1.27 ml, 9.15 mmol) was added dropwise to a stirred solution containing 1,2,4-triazole (820 mg, 11.8 mmol) and methylphosphonyl dichloride (600 mg, 4.5 mmol) in dry acetonitrile (90 ml). The mixture was stirred for one hour at room temperature. Then anhydrous adenosine (1 g, 1.9 mmol) dissolved in dry pyridine (10 ml) was added. After 4 hours of stirring at room temperature, a solution of triethylamine (1.7 ml), water (0.6 ml) and pyridine (4 ml) was added dropwise. Afterwards quenching was completed with 5% aq. NaHCO$_3$ the mixture was evaporated under vacuum to a small volume. The product in the concentrated aqueous solution was purified by reverse-phase chromatography using a column of LiChroprep RP8$^R$ and eluting with water. Fractions containing the product were collected and passed through a column of DOWEX 50W-X8$^R$,Na+ form. Water evaporation gave 350 mg of the title compound. Title HPLC: 99.0% (254 nm) PMR (200 MHz, DMSO): δ=8.41, 8.16(2s, 2H, adenine); 7.11(bs, 2H, NH$_2$; 6.10 (bs, 1H, OH); 5.89 (d, J=5.4 Hz, 1H, H1'); 5.80 (bs, 1H, OH); 4.56 (dd, J=3.8, 5.4 Hz, 1H, H2'); 4.25 (dd, J=3.3, 3.8 Hz, 1H, H3'); 3.99 (m, 1H, H4'); 3.79 (m, 2H CH$_2$ 5'); 0.94 (d, J=15.9 Hz, 3H, P-CH$_3$)

Preparation B

Methylphosphonyl dichloride (530 mg, 4 mmol) in 5 ml of triethylphosphate was added dropwise to a suspension of adenosine (540 mg, 2 mmol) in triethylphosphate (5 ml) kept at 0° C. The reaction mixture was stirred for 6 hours at 0° C. The mixture was quenched by adding 100 ml of 0.1M aqueous solution of triethylammonium bicarbonate (TEAB) at 0° C. The resulting solution was percolated through a IRA 93 column (30×5 cm). The column containing the product was washed by eluting with water, then the product was eluted with 0.1M aqueous TEAB. The solution was evaporated under vacuum to dryness, the residue was dissolved in water, purified by reverse-phase chromatography (RPS) and passed through a column of DOWEX 50W-X8, Na+ form. Water evaporation gave 200 mg of the title compound, showing the same analytical data of preparation A.

Preparation C

Carbonyldiimidazole (3.34 g, 20 mmol) was added to a solution of adenosine (2.67 g, 10 mmol) in dry DMF (20 ml). The solution was stirred for 4 hours, then diluted with saturated NaCl aqueous solution and extracted several times with ethyl acetate. Organic phase was dried (Na$_2$SO$_4$) and evaporated under vacuum and the residue was crystallized from diethylether giving solid adenosine 2'3' cyclic carbonate. Triethylamine (6.8 ml, 49 mmol) was added dropwise to a solution of methylphosphonyldichloride (3.25 g, 24.4 mmol) and 1,2,4-triazole (4,4 g, 63.6 mmol) in dry acetonitrile (50 ml). After stirring for 15 minutes, all the obtained amount of adenosine 2',3' cyclic carbonate dissolved in dry pyridine (50 mg) was added dropwise to this solution and the mixture was stirred for 1 hour at room temperature.

Afterwards a mixture of triethylamine (9 mg), water (3 ml) and pyridine (20 ml) was added and the reaction mixture was diluted with 5% aq. sodium bicarbonate. The aqueous solution was concentrated under vacuum and chromatographed through a LiChroprep RP-8 column eluting with water. Fractions containing the product were collected and percolated through a column of DOWEX 50W-X8, Na+ form.

The aqueous solution was evaporated obtaining 1.8 g of the title compound showing the same analytical data of preparation A.

Preparation D

Diphenylcarbonate (17 g, 79.4 mmol) was added to a solution of adenosine (10 g, 37.4 mmol) and phenol (3.4 g, 3.64 mmol) in dimethylformamide (50 ml). The suspension was heated for 1 hour at 150° C. The mixture was diluted with diethylether (2 liters) and the precipitate (adenosine 2'3' cyclic carbonate) was filtered.

Triethylamine (35.8 mg, 248 mmol) was added dropwise to a soution of methylphosphonyldichloride (15.26 g, 114.7 mmol) and 1,2,4- triazole (16.33 g, 236.7 mmol) in acetonitrile (200 ml). The solution was stirred for .1 hour at room temperature. The obtained adenosine 2'3' cyclic carbonate was dissolved in dry pyridine (200 ml) and added dropwise to the solution. The reaction mixture was stirred for 4 hours at room temperature and then a mixture of triethylamine (45 ml), water (24 ml) and pyridine (50 ml) was added dropwise. All the organic solvents contained in the mixture were evaporated under vacuum and the residue was chromatographed on a LiChroprep RP-8 column eluting with water. Fractions containing the product were collected, percolated through DOWEX 50W-X8, Na+ form - Water evaporation under vacuum gave 7.5 g of the title compound showing the same analytical data of preparation A.

Preparation E

Triethylamine (1.36, 9.8 mmol) was added dropwise to a solution of methylphosphonyldichloride (650 mg, 4.88 mmol) and 1,2,4-triazole (880 mg, 12.72 mmol) in dry acetonitrile (10 ml) and the solution was stirred for 15 minutes. 2'3'-0,0-bis (tert-butyldimethylsilyl) adenosine (obtained by standard procedure, 990 mg, 2 mmol) was dissolved in dry pyridine (10 ml) and added dropwise to the solution that was then stirred for 45 minutes at room temperature. The reaction mixture was quenched by adding a mixture of triethylamine (1.8 ml), water (0.6 ml) and pyridine (4 ml) and then diluted with a 5% aqueous solution of sodium bicarbonate. The aqueous phase was extracted with chloroform several times. The organic extracts were evaporated and the residue dissolved in tetrahydrofuran (10 ml). Tetrabutylammonium fluoride (1.2 g, 3.8 mmol) was added to the last solution that was then stirred for 30 minutes at room temperature. The reaction mixture was quenched with 0.1M aqueous triethylammonium bicarbonate and washed with methylene chloride. The aqueous phase was concentrated under vacuum and then chromatographed on reverse-phase (LiChroprep RP-8) eluting with water. Fractions containing the product were collected and passed through a column of DCWEX 50W-X8, Na+ form. The aqueous solution was evaporated under vacuum obtaining 600 mg of the title compound showing the same analytical data of preparation A.

Preparation F

Triethylamine (5 ml, 33.5 mmol) was added dropwise to a solution of methylphosphonyldichloride (2.15 g, 15.8 mmol) and 1,2,4 triazole (2.3 g, 33.3 mmol) in dry acetonitrile (30 ml). After stirring 1 hour at room temperature, 6-N,N-2',3'-0,0- tetrabenzoyladenosine (obtained by known procedure, 3.6 g, 5.27 mmol) dissolved in dry pyridine (10 ml) was added dropwise and the mixture stirred for 4 hours at room temperature. 0.1M aqueous solution of triethylammonium bicarbonate (250 ml) was added and the mixture was extracted with methylene chloride (3×100 ml). The organic phase was evaporated under reduced pressure, the residue was dissolved in dioxane (50 ml) and stirred with 30% aq. NH$_4$ OH (450 ml) for 12 hours at room temperature. The aqueous solution was evaporated under vacuum to dryness. The residue was washed with diethylether and purified by reverse phase chromatography on a column of LiChroprep RP-8 eluting with water. Fractions containing the product were collected and percolated through a column of DOWEX 50 W-X8, Na+ form. Evaporation under vacuum of the aqueous solution gave 1.3 g of the title compound, showing the same analytical data of preparation A.

EXAMPLE 2

5′-O-(P-isopropyloxy-P-methylphosphonyl) adenosine (FCE 26395)

Dry isopropanol (160 μl, 2 mmol) dissolved in dry pyridine (20 ml) was added dropwise to a solution of methylphosphonyldichloride (250 ml, 2 mmol) in dry pyridine (20 ml) and the mixture was stirred for 4 hours at room temperature. Then a suspension of adenosine (500 mg, 1.8 mmol) in dry pyridine (20 ml) was added to the mixture, that was then concentrated under vacuum to 10 ml and stirred for 12 hours at room temperature. The reaction was quenched with 5% aqueous sodium bicarbonate (100 ml). The mixture was evaporated under vacuum and the residue was chromatographed on a LiChroprep RP-8 column eluting with MeOH-$H_2O$ 2:8, obtaining 140 mg of 5′-O-(P-isopropyloxy-P-methylphosphonyl) adenosine as a mixture of diastereomers at P in the ratio 1:1. Title HPLC: 96% (254 nm). PMR (200 MHz, DMSO): δ=8.34, 8.16 (2s, 2H, adenine); 7.45 (bs, 2H, N$\underline{H}$H$_2$); 5.91 (d, J=5.1 Hz, 1H, H1′); 5.2–5.7 (bs, 2 OH); 4.63 (m, 1H, H-2′); 4.50 (m, 1H, CH$_3$-C$\underline{H}$-CH$_3$); 4.23 (m, 2H, H-3′H-4′); 4.0–4.2 (m, 2H, $\overline{CH}_2$-5′); 1.40, 1.38 (2d, J=17.3 Hz, 3H, CH$_3$-P, 2 diastereomers); 1.20 (m, 6H, CH(C$\underline{H}_3$)$_2$)

EXAMPLE 3

Adenosine 5′-n.butylphosphonate sodium salt (FCE 26231A)

N-butylphosphonyldichloride (230 ml, 1.63 nmol) was added to a solution of 6-N-benzoyl-2′-3′-O-(tetraisopropyldisiloxane-1,3-diyl)adenosine (obtained by known procedure, 1 g, 1.63 mmol) in dry pyridine (15 ml), kept at 0° C. The reaction mixture was stirred for 2 hours allowing the temperature to go up to room temperature.

0.1M aqueous solution of triethylammonium bicarbonate (25 ml) was added and, after dilution with water (50 ml), the mixture was extracted with methylene chloride (3×50 ml). Solvent was evaporated under vacuum from the organic phase. The residue was dissolved in dioxane (25 ml) and treated with aq. 30% NH$_4$OH (75 ml) for 1 night at room temperature. The aqueous solution was washed with diethylether (3×50 ml) and water was evaporated under vacuum. The residue was purified by reverse phase chromatography on a LiChroprep RP-8 column eluting with water and then with a gradient of methanol from 0 to 10%. Evaporation of the solvent from the proper fractions gave a concentrated aqueous solution that was passed through a column of Dowex 50W-X8,Na+ form. Water was evaporated under vacuum obtaining 240 mg of the title compound.

Title HPLC: 95.7% (254 nm) PMR (200 MHz, DMSO): δ=8.41, 8.12 (2s, 2H, adenine); 7.07 (bs, 2H, NH$_2$); 5.88 (d, J=5.4 Hz, 1H, H-1′); 4.55 (dd, J=5.3, 5.4 Hz, 1H, H-2′); 4.22 (dd, J=3.7, 5.3 Hz, 1H, H-3′); 4.00 (m, 1H, H-4′); 3.82 (m, 2H, C$\underline{H}_2$-5′); 1.4–1.1 (m, 6H, CH$_3$(CH$_2$)$_3$ P); 0.77 (t, J=7.0 Hz, 3H, C$\underline{H}_3$ (CH$_2$)$_3$P).

TABLE 1

FCE 25148: IN VITRO ACTIVITY

| VIRUS | CELL | CYTO-TOXICITY T.C. ID$_{50}$ (MG/ML) | ANTIVIRAL ACTIVITY A.I. (TCID$_{50}$/IVID$_{50}$) |
|---|---|---|---|
| INFLUENZA | BHK | 400 | 11 |
| RESPIRATORY SYNCYTIAL | HEP | 360 | 18 |
| SEMLIKI FOREST | HEP | 360 | 15 |
| COXSACKIE | HEP | 360 | 6 |
| COL. SK | L 929 | 270 | 5 |
| VACCINIA | HEP | 360 | 5 |

TABLE 2

IN VIVO ACTIVITY OF FCE 25148A IN MICE INFECTED WITH INFLUENZA VIRUS

| COM-POUND | DOSE MG/KG | DOSE MCG/MOUSE | ROUTE | % PROTECTION (LUNG LESIONS) TEST |
|---|---|---|---|---|
| FCE 25148A | 6.25 | 125 | I.N. | 24.5* |
| " | 1.6 | 31 | " | 22.5* |
| " | 0.4 | 7.8 | " | 22.5* |
| " | 0.1 | 1.9 | " | — |
| " | 0.025 | 0.5 | " | — |
| RIBAVIRIN | 1.6 | 31 | " | 15° |
| " | 100 | 2000 | P.OS | 27* |

*° p < 0.025 (WILCOXON TEST)
*= p < 0.01 (WILCOXON TEST)

TABLE 3

IN VIVO ACTIVITY OF FCE 25148A IN MICE WITH ENCEPHALITIS INDUCED BY SEMLIKI FOREST VIRUS

| | I.C. TREATMENT | | |
|---|---|---|---|
| | DOSE (MG/KG) | CONCENTRATION (MCG/ML) | % PROTECTION (MORTALITIES) RANGE |
| FCE | 3.5 | 2000 | 95–100 |
| | 1.75 | 1000 | 78–100 |
| | 0.875 | 500 | 58–95 |
| RIBAVIRIN | 5.25 | 3000 | 0–63 |
| | 2.6 | 1500 | 0–53 |

We claim:

1. A method of treating a disease caused by an RNA virus selected from the group consisting of Respiratory syncytial, Semliki Forest, Coxsackie, Vaccinia, Columbia SK and influenza, comprising administering to an animal in need thereof a therapeutically effective amount of a compound of formula (I):

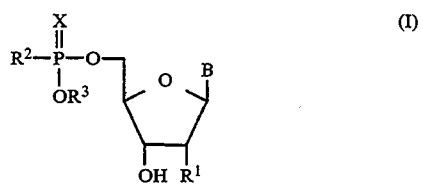

wherein B is adenine; R$^1$ is hydroxyl or hydrogen; R$^2$ is a linear or branched alkyl of up to twenty carbon atoms; and R$^3$ is a linear or branched alkyl of up to twenty carbon atoms, hydrogen, or a cation.

2. The method of claim 1, wherein R$^2$ is methyl, ethyl, propyl, isopropyl or n-butyl.

3. The method of claim 1, wherein R$^3$ is methyl, ethyl, propyl, isopropyl, n-butyl, sodium, potassium or ammonium.

4. The method of claim 1, wherein the compound of formula (I) is selected from the group consisting of 5'-methylphosphonyladenosine, the sodium salt of 5'-methylphosphonyladenosine, 5'-O-(P-isopropyloxy-P-methylphosphonyl)adenosine, 5'-n-butylphosphonyladenosine and the sodium salt of 5'-n-butylphosphonyladenosine.

5. The method of claim 1, wherein said RNA virus is influenza.

6. The method of claim 1, wherein said RNA virus is Semliki Forest.

7. The method of claim 1, wherein said RNA virus is selected from the group consisting of Respiratory syncytial, Semliki Forest, Coxsackie, Vaccinia and Columbia SK.

* * * * *